United States Patent [19]

Hewitt et al.

[11] Patent Number: 4,945,577
[45] Date of Patent: Aug. 7, 1990

[54] VENTILATED SPLASH GOGGLE

[75] Inventors: Charles D. Hewitt, Houston, Tex.; Paul B. Specht, Wilmette, Ill.

[73] Assignee: Encon Safety Products, Inc., Houston, Tex.

[21] Appl. No.: 618,333

[22] Filed: Jun. 7, 1984

[51] Int. Cl.⁵ .............................................. A61F 9/02
[52] U.S. Cl. ............................................... 2/437
[58] Field of Search ............... 2/436, 426, 428–431, 2/437, 439–445

[56] References Cited

U.S. PATENT DOCUMENTS

| | | | |
|---|---|---|---|
| 1,670,638 | 5/1928 | Shindel | 2/437 |
| 3,000,011 | 9/1961 | Sterne | 2/436 |
| 3,141,172 | 7/1964 | Hirschmann | 2/436 |
| 3,418,658 | 12/1968 | Danico | 2/436 |
| 3,638,240 | 2/1972 | Militello | 2/437 |
| 4,027,342 | 6/1977 | Hirschmann | 2/436 |
| 4,264,988 | 5/1981 | Specht | 2/431 |

Primary Examiner—Peter Nerbun
Attorney, Agent, or Firm—John R. Kirk, Jr.

[57] ABSTRACT

A protective splash goggle which includes a new two piece labyrinthian vent which allows the circulation of air while preventing the passage of splashed liquids and further including a curved lens which includes a lens mounting providing functional gaps which resists separation of the lens from the frame upon distortion of the goggle.

16 Claims, 2 Drawing Sheets

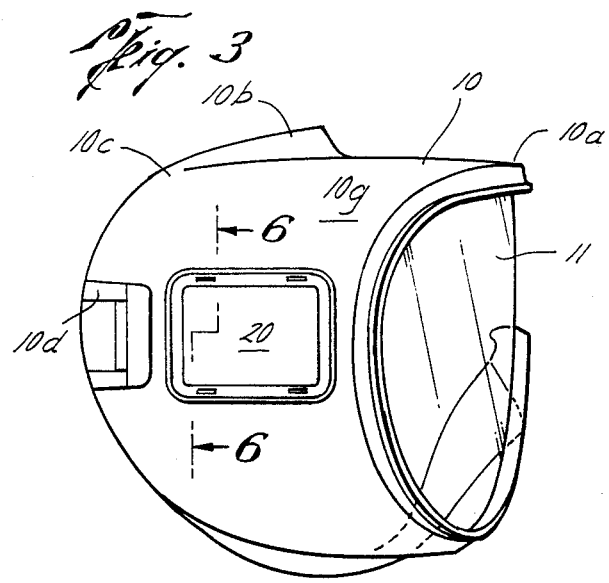
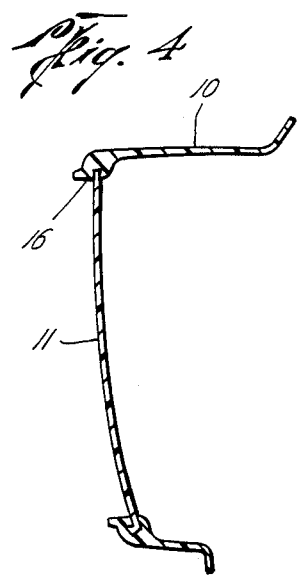
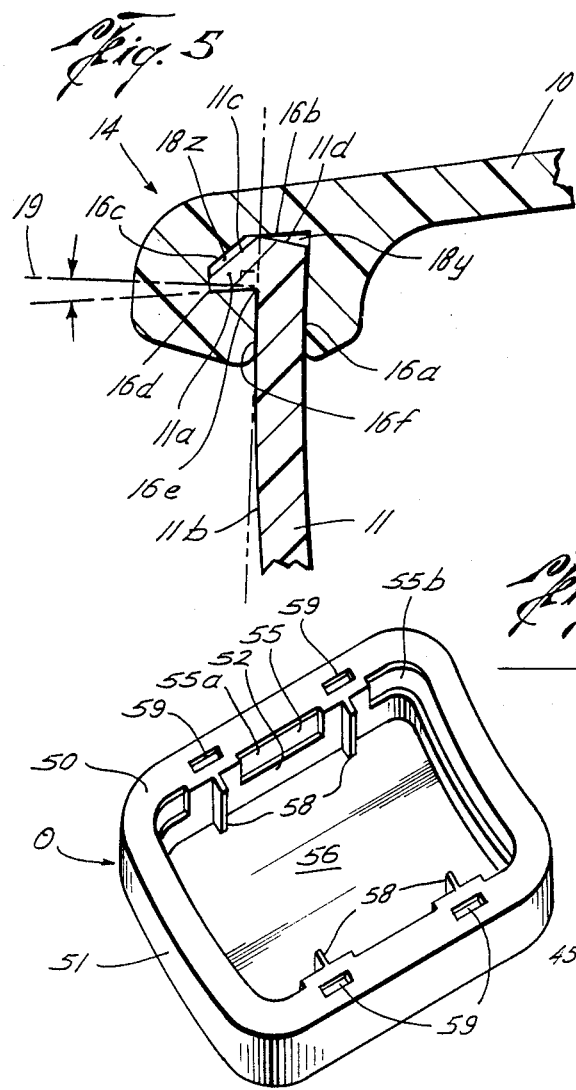
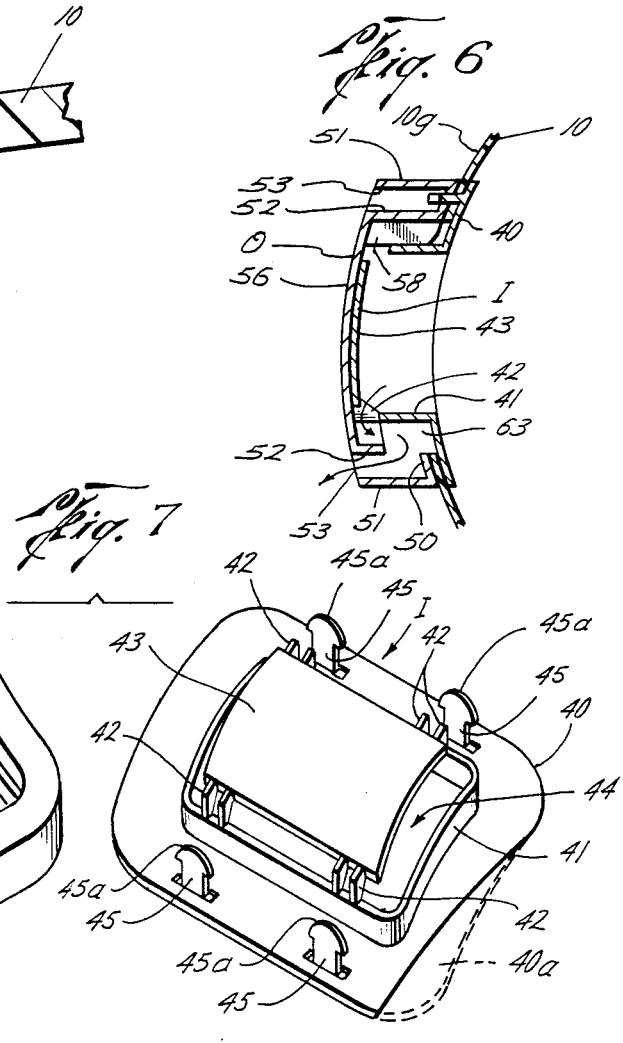

VENTILATED SPLASH GOGGLE

FIELD OF THE INVENTION

The present invention relates to protective goggles for protecting the eye area of the wearer from chemical splash and other hazardous materials.

DESCRIPTION OF THE PRIOR ART

The purpose of protective goggles is to shield the eye area of the wearer from outside material while not interfering with vision or comfort. In industry, goggles are used extensively to protect against chemical splash or other hazardous liquids. Protective goggles are also used in sports such as skiing or motorcycling.

For the purposes of describing prior art, goggles may be classified into three groups: goggles without ventilation; goggles with openings for ventilation; and goggles with shielded openings to at least in part prevent the entry of deleterious materials such as chemical splash into the protected eye region of the wearer. The protective goggle of this invention is particularly directed to the latter category of goggles.

There are a substantial number of patents which disclose goggles of various types and styles, but have no ventilation openings. A list of such goggles in chronological order are as follows: U.S. Pat. Nos. Design 138,545; Design 140,312; 2,387,821; 2,589,575; Design 171,762; 2,688,135; 2,706,815; Design 175,015; Design 177,581; 2,770,807; Design 182,463; Design 186,792; Design 207,127; Design 207,796; Design 214,258; 3,484,156; 3,505,680; and Design 232,983. This list of patents directed to goggles without ventilation means is not exhaustive.

A second group of patents relates to patents having exposed ventilation openings in various configurations and sizes: U.S. Pat. Nos. Design 136,379; 2,368,750; Design 140,805; Design 142,221; 2,406,998; 2,422,534; 2,573,722; Design 166,231; Design 166,257; 2,598,265; 2,603,785; 2,608,687; 2,617,100; Design 168,936; Design 168,988; 2,645,775; 2,680,846; 2,680,882; Design 176,309; 2,773,260; Design 180,892; Design 181,456; 2,877,462; 2,903,700; 2,914,770; 2,936,459; 2,979,728; 3,012,248; Design 204,099; 3,274,614; 3,298,031; 3,368,221; 3,395,406; 3,517,393; 3,591,846; Design 223,983; 3,718,937; 3,896,496; 3,931,646; and Design 242,666. This list of patents in this second category is not exhaustive.

The third category, goggles with shielded openings, include U.S. Pat. No. 1,670,638 which disclosed a goggle assembly which included a vent made up of two cupped shaped parts and a lens held in place by a compressible flexible retaining ring. U.S. Pat. No. 3,000,011 disclosed safety goggles which included sets of openings each surrounded by an outwardly directed flange to provide a dam or barrier against flow of moisture into the goggle frame openings. The flange surrounded openings were covered with a cap or shield to prevent direct entry of undesirable materials. U.S. Pat. No. 2,877,463 disclosed a goggle frame having an oblong opening covered by an oblong panel having alternatively spaced flanges for allowing only indirect entry of air. U.S. Pat. No. 3,141,172 disclosed a ventilated goggle which included a tubular base which extended outwardly through an opening in the frame and had a ventilated cap mounted thereover. U.S. Pat. No. 3,418,658 disclosed a circular ventilating cap design to prevent the entry of foreign matter through the cap opening into the goggle frame opening over which the cap was mounted. U.S. Pat. Nos. 3,638,240; 3,081,461; 3,708,224; 2,715,223; 2,399,991 and 2,395,297 also disclosed ventilation systems for goggle frame openings that were at least partly shielded. U.S. Pat. No. 4,027,342 disclosed a two part goggle ventilator wherein a single pin was used to lock cup shaped elements together wherein the air path led through the side wall of the outside piece up through the end of the inner piece.

SUMMARY OF THE INVENTION

The present invention relates to new and improved ventilators and a lens mount for splash goggles. The splash goggles of the present invention provide high resistance to separation of the lens from the goggle frame in an easily and inexpensively assembled unit. The splash goggles according to the present invention include a two piece ventilation element which is easily and inexpensively formed and assembled which provides ventilation while preventing the entry of splashed fluids into the protected area around the eyes of the wearer.

The goggle lens of the present invention is a section of a sphere. The lens includes a lip extending from a convex outer surface which has an edge perpendicular to a plane. The edge of the lens is made up of two planar surfaces at an obtuse angle.

The goggle frame of the present invention is formed to conform to the facial contours of the wearer, enclosing the eye area. The lens mount in the front of the goggle frame is a groove having a tongue which receives the lip of the lens. The interior surface of the lens mounting groove is formed by a number of planes nonparallel with those on the lens edge so that functional gaps remain between the lens edge and the frame after assembly.

The vent of the present invention is a two piece device to be attached to the goggle frame through an opening. The inner element includes a hollow upright extending from a flange having a cap supported above the upright by a plurality of pairs of fingers. The outer element includes a flange having an exterior wall, an interior wall having openings and a cap sealing the interior wall. The inner element flange includes tabs which snap through slots in the outer element flange through openings in the goggle frame adjacent the primary opening. The telescoping arrangement of the inner and outer elements provide a tortuous air path which resists the passage of splashed liquids while allowing sufficient air passage for ventilation.

BRIEF DESCRIPTION OF THE DRAWINGS

FIG. 3 is a side view taken along line 3—3 of FIG. 1.

FIG. 4 is a sectional view taken along line 4—4 of FIG. 1.

FIG. 5 is a sectional view taken along line 5—5 of FIG. 1 depicting the mounting means for the lens.

FIG. 6 is a sectional view taken along stepped line 6—6 of FIG. 3 showing the labyrinth of the assembled vent.

FIG. 7 is an exploded perspective view of the parts making up the vent of FIG. 6.

DESCRIPTION OF THE PREFERRED EMBODIMENT

Figure 1:
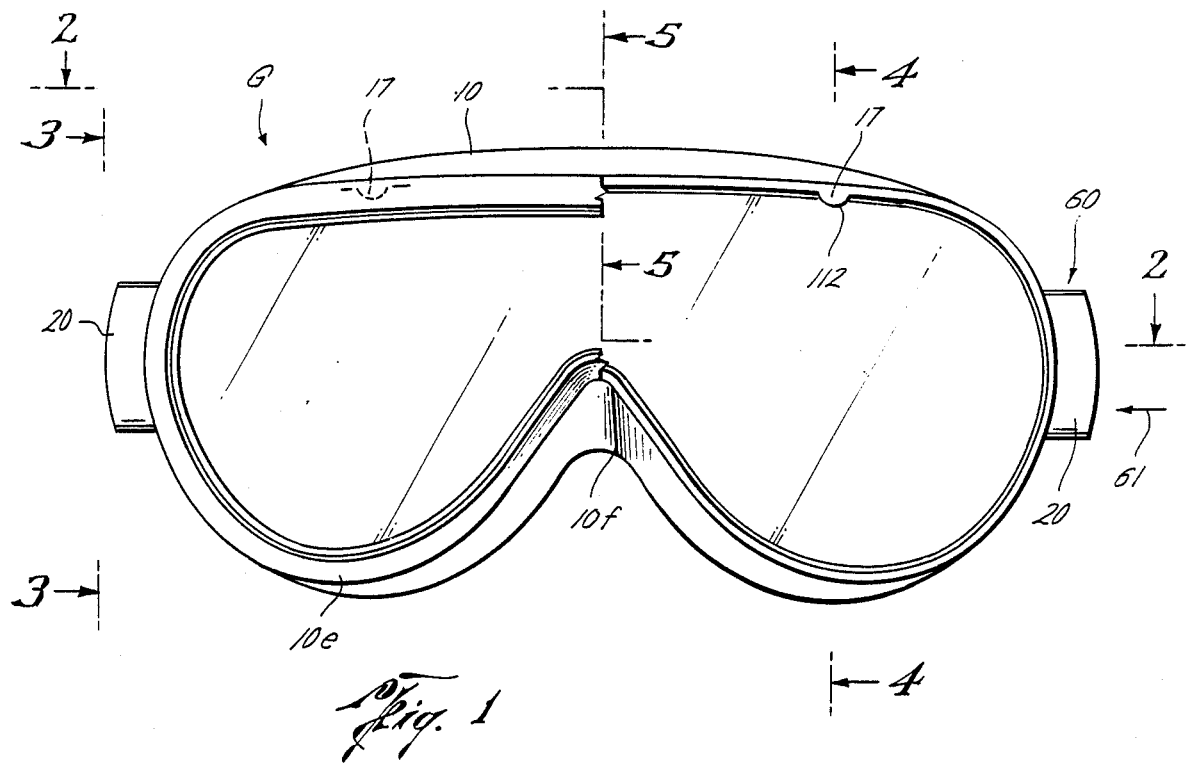
FIG. 1 is a front view of the present invention with a partial sectional view taken along the continuous groove for mounting the lens in the frame of one-half of the goggle.

The protective goggle G of the present invention is useful in industry in hazardous environs or as a sports goggle for sports such as skiing. Industrial use of the goggles G of the present invention would include activities such as grinding, polishing, sanding or use in chemical plants where workers may be subject to chemical splash or other hazardous materials. The goggle G may also be used for general purpose eye protection where it is desirable to prevent the entry of foreign materials into the region protected by the goggles while allowing for air flow into and out of the protected region.

The protective goggle of the present invention includes a frame generally designated as 10 which mounts a lens generally designated as 11. The goggle frame 10 may be made of a material such as rubber or plastic which provides a semi-rigid goggle frame which can be easily formed such as by molding. The goggle frame includes a front portion 10a which includes mounting means 14 (FIG. 5) for the lens 11. The goggle frame 10 has a rear portion 10b formed integrally with front frame portion 10a. The rear frame portion 10b terminates in a rear periphery or contour edge 10c designed to fit against the facial area of the wearer which surrounds the wearer's eyes. Basic peripheral configuration of the rear portion 10b is well known in the art and fits snugly against the face of the wearer and the semi-rigid frame 10 conforms to the coutour of the face of the wearer to prevent entry of hazardous liquids into the protected area around the eyes. The goggle frame 10 further includes strap connecting studs 10d which may be integrally formed with the goggle frame for mounting a strap (not shown) for positioning about the head of the wearer to hold goggle G in place as well known in the art.

The lens mounting means 14 (FIG. 5) is formed by a continuous groove 16 formed in the interior of the front goggle portion 10a. The groove 16 follows the curvature of the front portion of the goggle frame 10a which is substantially convex when viewed from the top and has two lower curved portions 10e which are connected by an inverted V-shaped portion 10f fitting over the bridge of the wearer's nose. This configuration is well known in the goggle art.

The lens mounting means 14, as shown in FIG. 5, involves the interior configuration of groove 16 which includes a rear wall 16a, a top surface formed by two planar segments 16b and 16c intersecting each other at an obtuse angle, a front wall 16d, shoulder 16e formed by planes intersecting at an acute angle as will be more fully described hereinbelow and front wall 16f. Groove 16 includes two detents 17 (FIG. 1) which extend into groove 16 in line with notches 11z in lens edge 11c. Utilization of the frame detents 17 in cooperation with the lens notches 11z provides for ease of alignment of the lens 11 and goggle frame 10.

Figure 2:
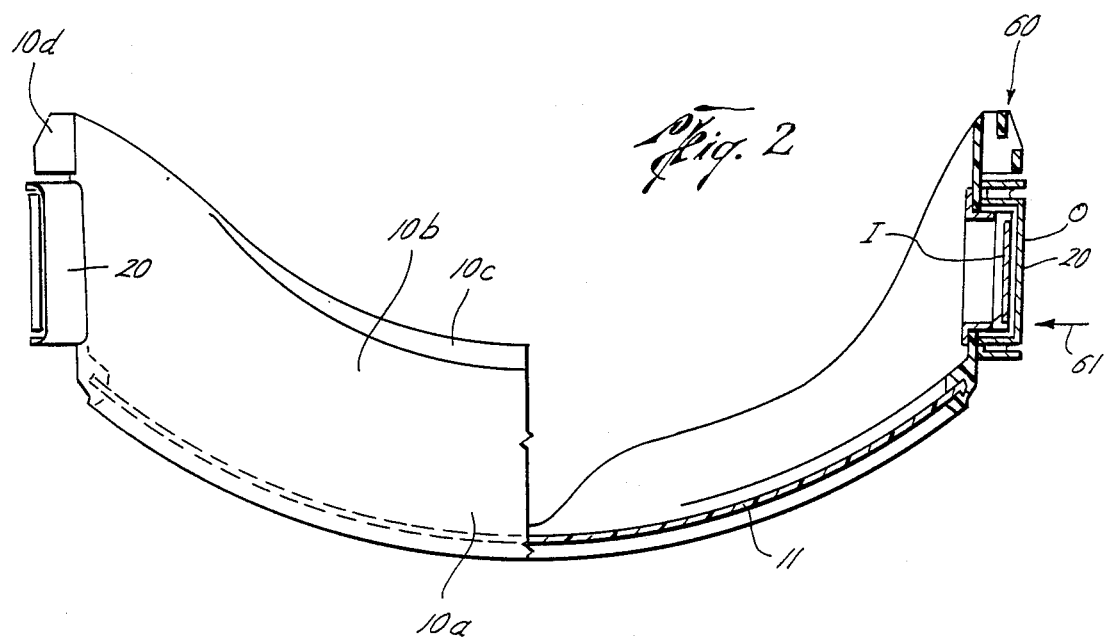
FIG. 2 is a sectional view taken along stepped line 2—2 of FIG. 1.

The lens 11 is formed from a section of a sphere thereby being convex when viewed from both the top and side and having the same radius of curvature as the front edge of the front portion 10a and groove 16 of the goggle. The utilization of a spherical segment for the lens provides a lens surface which has the same radius of curvature in the vertical and horizontal directions as viewed in FIGS. 2 and 4. Lens 11 includes a lip 11a extending from the periphery outer surface 11b of the lens 11. As viewed in section in FIG. 5, lip 11a forms an acute angle X with a line 19 normal to the lens surface 11b at the point of intersection of lip 11a and lens surface 11b. The lens edge 11c is defined by two planes 11d and 11e intersecting at an obtuse angle. Lens edge planes 11d and 11e are of such a dimension so as to not correspond to the dimensions of the planar segments 16b and 16c of goggle frame groove 16. Thus, upon location of the lens 11 in groove 16 as aligned by detents 17, the shoulder 16e of groove 16 contacts or is adjacent to lip 11a of lens 11 thereby retaining lens 11 in frame 10. The non-parallel position the lens edge 11c and the planar segments 16b and 16c result in functional voids or gaps 18y and 18z remaining between the lens edge 11c and the goggle frame 10. The result is that the resistance to separation of the lens 11 from goggle frame 10 is greatly increased even upon extreme deformation of the completed assembly. Previous frame and lens assemblies wherein the lens rim surfaces fit against corresponding, parallel frame groove surfaces resulted in poor structural stability when the goggle was deformed with the result that the lens would often "pop out" of the frame at unexpected and inconvenient times.

The preferred embodiment of the goggles of the present invention further includes vent assemblies 20, one mounted on each side 10g of goggle frame 10. Each vent assembly 20 provides for ventilation of the goggles to prevent fogging of the lens or wearer discomfort while preventing the entry of splashed liquids into the protected area. Shown in detail in FIGS. 2, 6 and 7, the vent assembly 20 include an inner element I and an outer element O. The telescopic alignment of the inner element I and outer element O through an opening in goggle frame 10 creates a tortuous path, or labyrinth, which prevents the passage of splashed liquids while allowing air to flow into or out of the interior region protected by the goggle G.

Inner element I includes a flange or ledge 40 preferably of substantially rectangular, annular shape having a cross-sectional curvature (FIG. 1) corresponding to the side 10g of the goggle frame 10. A corner 40a of flange 40 may be removed in order to provide clearance between the flange 40 and goggle lens mounting means 14. Extending from flange 40 is hollow, rectangular upright or wall 41 having a cross-sectional size corresponding to that of a hole in goggle frame 10. Supported above hollow upright 41 on four pairs of support fingers 42 is cap 43. The number of pairs and orientation of support fingers is not critical but four is preferred to give optimum stability to the vent. Cap 43 is substantially the size of the opening of hollow upright or wall 41 and is supported above hollow upright 41 so as to create a rectangular gap or air space 44 to allow the passage of air. Extending from flange 40, adjacent and parallel to hollow upright 41 are tabs 45. Tabs 45 include enlarged portion heads 45a to interlock with slots in outer element O as will be more fully described hereinbelow.

Outer element O includes flange 50 of substantially rectangular shape having a cross-sectional curvature corresponding to the outside of the goggle frame and having a configuration for alignment with the flange or ledge 40 of inner element I, with the frame side therebetween. Extending from the outside edge of flange 50 is exterior wall 51. Extending from the inside edge of flange 40 is interior wall 52 of substantially the same height as exterior wall 51 thus forming rectangular channel 53. Generally rectangular opening or slot 55 is provided at the intersection of flange 50 and interior wall 52 to allow the passage of air. Interior wall 52 is sealed by cap or cover 56. Extending from the intersection of inner wall 52 and cap 56 are alignment braces or members 58. Upon assembly of the vent assembly 20, alignment braces 58 mesh and fit between support fingers 42 of inner element 40 to ensure proper positioning of the elements. Flange 50 of outer element O includes slots 59 corresponding to tabs 45 of inner element I of a size so that the heads 45a of tabs 45 snap through slots 59 thereby locking the elements together. The opening 55 includes opposing side slots such as 55a and opposing end slots such as 55b which cooperate to make the opening 55 a generally rectangularly shaped opening or slot.

In assembly of the vent assembly 20, inner element I is located so that hollow upright 41 extends through a hole in goggle frame 10 having the cross-sectional area of hollow upright 41, and tabs 45 extend through adjacent openings through the frame . Outer element O is located so that slots 59 align with tabs 45 and the vent elements are snapped together. Vent assembly 20 is thus supported on goggle frame 10 by the contact between flange 50 of the outer element O and flange 40 of the inner element I with the goggle frame 10. In this manner, the inner and outer elements I and O cooperate to provide a continuous outer rectangular wall 51 which protects against entry of fluid splash from a direction such as 60 in FIG. 1 which would be in a vertical plane if the goggles are positioned as illustrated in FIG. 1. The continuous outside- wall 51 also prevents entry of splash rolling along the outside surfaces of the frame side 10g from any direction. The vent assembly 20 further provides a generally rectangular, continuous channel 53 which faces the side of the goggle so that only fluid splash directed generally along arrow 61 (FIG. 1) would enter the channel 53. However, fluid entering the channel 53 could only flow inwardly through slots 55a and 55b, which are aligned with wall 41 of inner element I which prevents fluid from splashing into the interior of the goggle. Yet, a labyrinth or tortuous air path is provided through channel 53 and slots 55 of outer member O, through the annular area 63 between outer element wall 52 and inner element wall 41 and into the goggle through rectangular air spaces 44 of inner element I.

The preferred embodiment of the ventilated splash goggles of the present invention includes a new and improved lens shape and mounting system which results in a low cost, easily assembled goggle highly resistant to separation of the lens from the goggle frame and a vent assembly which can be easily and expensively manufactured, such as by molding of plastic and assembled which provides ventilation of the goggle interior while resisting the passage therethrough of splashed chemicals.

The foregoing disclosure and description of the invention are illustrative and explanatory thereof, and various changes in the size, shape, combination and materials as well as in the details of the illustrated construction may be made without departing from the spirit of the invention. For example, goggles G may include only one or both features of the lens mounting means 14 or the ventilator assembly 20. An additional advantage of the goggles G is that the use of a lens having a curved shape eliminates the tunnel vision and distortion found in many soft body safety and chemical goggles.

What is claimed is:

1. A protective goggle for protecting the eye area of the wearer which comprises:
    a goggle frame having front lens mounting means and a rear edge adapted to conform to the wearer's facial contour and means to hold the goggle frame to the wearer's face enclosing the wearer's eye area;
    a goggle lens mounted by said front lens mounting means with said goggle frame; and
    vent means mounted with said goggle frame to allow the circulation of air into and out of the interior of the goggle while inhibiting the entry of liquids into the goggle including an inner element for extending through a frame opening in the goggle frame and an outer element for mounting over said inner element, said inner and outer elements cooperating to provide attachment means for mounting said inner and outer elements together with said opening in said frame, said outer element including a continuous exterior wall to prevent the entry of fluid in a direction against said exterior wall and further including an interior wall cooperating with said exterior wall to provide a continuous channel behind said exterior wall, said inner and outer elements cooperating to provide means to prevent the further passage of splash fluid from said continuous channel into the interior of said goggle while allowing for the circulation of air into said goggle.
2. The structure set forth in claim 1, including:
    said inner and outer elements cooperating to provide an indirect path from said continuous channel through said inner element into the interior of said goggle to thereby allow for the circulation of air into and out of said goggle through said inner and outer elements while preventing splash fluid from entering into said goggle.
3. The structure set forth in claim 1, including:
    said inner element including an annular ledge conforming to the interior of said goggle frame around said goggle frame opening, a hollow wall extending transversely from the interior of said ledge for extending through said goggle frame opening and having a cap mounted onto said hollow wall with air slots formed between said cap and said hollow wall; and
    said outer element comprising a ledge of the same general configuration as said ledge on said inner element and said interior wall having openings therein which are non-aligned with said slots in said inner element whereby a tortuous path for the circulation of air is provided between said inner and outer elements which prevents the passage of splash fluid from said continuous channel through said inner element into the goggle.
4. The structure set forth in claim 3, wherein said attachment means includes:
    said inner element ledge including means for extending through said goggle frame opening and into engagement with said corresponding ledge on said outer element in order to attach said inner and outer elements together and to said frame.
5. The structure set forth in claim 1, wherein said outer element includes:
    said continuous outer wall; and
    said inner wall spaced from said outer wall and having a bottom formed therebetween to provide a U-shaped, substantially continuous channel.
6. The structure set forth in claim 5, including:

said inner wall having openings therein to allow the passage of air, said openings being non-aligned with an upstanding wall of said inner element to prevent the passage of fluid into said goggle.

7. A protective goggle for protecting the eye area of the wearer which comprises:

a goggle frame having a rear shape conforming to the contour of the wearer's face including a top having a rim to rest above the wearer's eyes, a bottom edge to rest below the wearer's eyes including a nose piece cut out to rest on the wearer's nose and a front edge having a lens mounting means and sides including a means to hold the protective goggle against the wearer's face;

a goggle lens;

said lens mounting means including said goggle frame having a substantially continuous groove therein for receiving said goggle lens, said goggle lens having a mounting rim cooperating with said substantially continuous groove to provide distortion compensation means for mounting and maintaining said goggle lens in said groove;

said distortion compensation means including said mounting rim of said goggle and said substantially continuous groove in said goggle frame having non-parallel surfaces which provide functional gaps to allow relative movement between said frame groove surfaces and said goggle rim as said goggle frame distorts to thereby prevent said groove surfaces from pushing said goggle rim outwardly of said groove.

8. The structure set forth in claim 7, including:

said goggle lens having a radius of curvature as viewed from the top or bottom of the goggle frame; and said substantially continuous groove in said goggle frame having substantially the same radius of curvature as said goggle lens.

9. The structure set forth in claim 7, including:

said goggle lens having a peripheral ridge on said mounting rim which extends into said substantially continuous goggle frame groove in continuous engagement with said goggle frame groove.

10. The structure set forth in claim 7, wherein:

said goggle rim includes first and second planar surfaces which correspond with but do not align with first and second planar segments of said goggle frame groove to thereby create functional voids which allow for frame distortion without the planar segments of said goggle frame groove forcing said goggle lens outs of said goggle frame groove.

11. The structure set forth in claim 7, wherein:

said goggle lens is curved in transversely oriented directions.

12. The structure set forth in claim 7, wherein:

said goggle lens is a section of a sphere.

13. A protective goggle for protecting the eye area of the wearer, comprising:

a goggle frame having a rear shape conforming to the contour of the wearer's face including a top having a rim to rest above the wearer's eyes, a bottom edge to rest below the wearer's eyes including a nose piece cut out to rest upon the wearer's nose and a front edge having a lens mounting means and sides including means to hold the protective goggle against the wearer's face;

a goggle lens;

said lens mounting means and goggle frame cooperating to provide distortion compensation means for mounting and maintaining said goggle lens in said groove;

said distortion compensation means including said goggle frame having a substantially continuous mounting groove and said goggle having a substantially continuous mounting rim, said mounting rim of said goggle and said substantially continuous groove in said goggle frame having non-parallel surfaces providing functional gaps to allow relative movement between said goggle frame groove surfaces and said goggle rim as said goggle frame distorts to thereby prevent said groove surfaces from pushing said goggle rim outwardly of said goggle frame; and said goggle frame having mounted therewith vent means to allow the circulation of air into and out of the interior of the goggle while inhibiting the entry of liquids into the goggle including continuous wall means positioned outside the goggle frame to provide a barrier to the entry of fluid in a direction along the surface of said goggle frame and further including a continuous channel means for receiving splash fluid and preventing the further intrusion of splash fluid through said vent means.

14. The structure set forth in claim 13, including:

said vent means including inner and outer elements cooperating to provide attachment means for mounting said inner and outer elements together with an opening in said frame, said outer element including a continuous outside wall to prevent the entry of fluid in a direction against said wall and further including a continuous channel, said inner and outer elements cooperating to provide means to prevent the further passage of splash fluid from said continuous channel into the interior of said goggle while allowing for the circulation of air into said goggle.

15. The structure set forth in claim 14, including:

said inner and outer elements cooperating to provide an indirect path from said outer element channel through said inner member into the interior of said goggle to thereby allow for the circulation of air into and out of said goggle through said inner and outer members while preventing said splash fluid from entering into said goggle.

16. The structure set forth in claim 15, including:

said inner element including an annular ledge conforming to the interior of said goggle frame around a hole therein, a hollow wall extending transversely from the interior of said ledge for extending through said goggle frame opening and having a cap mounted onto said hollow wall member with air slots formed between said cap and said hollow wall member; and said element comprising a ledge of the same general configuration as said ledge on said inner element and having an exterior continuous wall and an interior continuous wall which cooperate to provide an interior channel, said interior wall having openings therein which are non-aligned with said slots in said inner member whereby a tortuous path for the circulation of air, is provided between said inner and outer elements which prevents the passage of splash fluid from said outer member channel through said inner member into the goggle.

* * * * *